United States Patent [19]
Wildman et al.

[11] Patent Number: 5,474,446
[45] Date of Patent: Dec. 12, 1995

[54] MINIATURE SELF-LOCKING LABIAL BRACKET WITH CAM-RELEASE CLOSURE MEMBER

[76] Inventors: Alexander J. Wildman, 2440 Willamette St., Eugene, Oreg. 97405; James F. Reher, 1256 N. Hamilton, Pomona, Calif. 91768; Lawrence P. Phaneuf, 17161 Elaine, Fontana, Calif. 92366

[21] Appl. No.: 271,031

[22] Filed: Jul. 6, 1994

[51] Int. Cl.⁶ ................................................. A61C 3/00
[52] U.S. Cl. ........................... 433/14; 433/10; 433/11
[58] Field of Search ........................... 433/8, 9, 10, 13, 433/14, 18

[56] References Cited

U.S. PATENT DOCUMENTS

| | | | |
|---|---|---|---|
| 4,149,314 | 4/1979 | Nonnenmann | 433/13 |
| 4,193,195 | 3/1980 | Merkel et al. | 433/13 |
| 4,427,381 | 1/1984 | Hall | 433/14 |
| 4,496,318 | 1/1985 | Connelly, Jr. | 433/14 |
| 4,565,526 | 1/1986 | Kawata et al. | 433/14 X |
| 5,094,614 | 3/1992 | Wildman | |
| 5,123,838 | 6/1992 | Cannon | 433/14 |
| 5,224,858 | 7/1993 | Hanson | 433/10 |
| 5,275,557 | 1/1994 | Damon | 433/14 X |
| 5,362,233 | 11/1994 | Thompson | 433/14 X |

*Primary Examiner*—Nicholas D. Lucchesi
*Attorney, Agent, or Firm*—Marger, Johnson, McCollom & Stolowitz

[57] ABSTRACT

A bracket having a closure slot extending through both sides of the bracket body across art archwire slot for a closure member to secure an archwire. The bracket body has an internal shoulder extending across one side of the closure slot. The closure member is a lengthwise-folded flat spring having a free end positioned and biased to engage the shoulder when closed, and including a ramp forming a cam at the distal end thereof. Pushing the closure member lengthwise in the closure slot with sufficient force depresses the free end to disengage it from the internal shoulder to slide the closure member to an open position. Intermediate retention ears are formed on the core of the closure member to engage opposite lateral sides of the closure slot when open. A bendable tab is formed in the bracket body to block the closure member from removal from one end of the closure slot after insertion therein. The bracket body has twin pairs of tie wings to provide dual modes of closure.

20 Claims, 2 Drawing Sheets

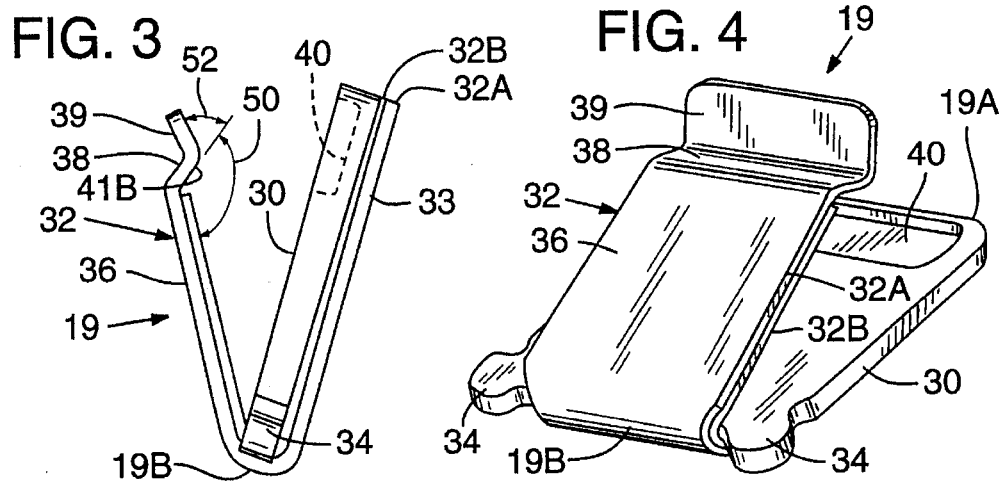
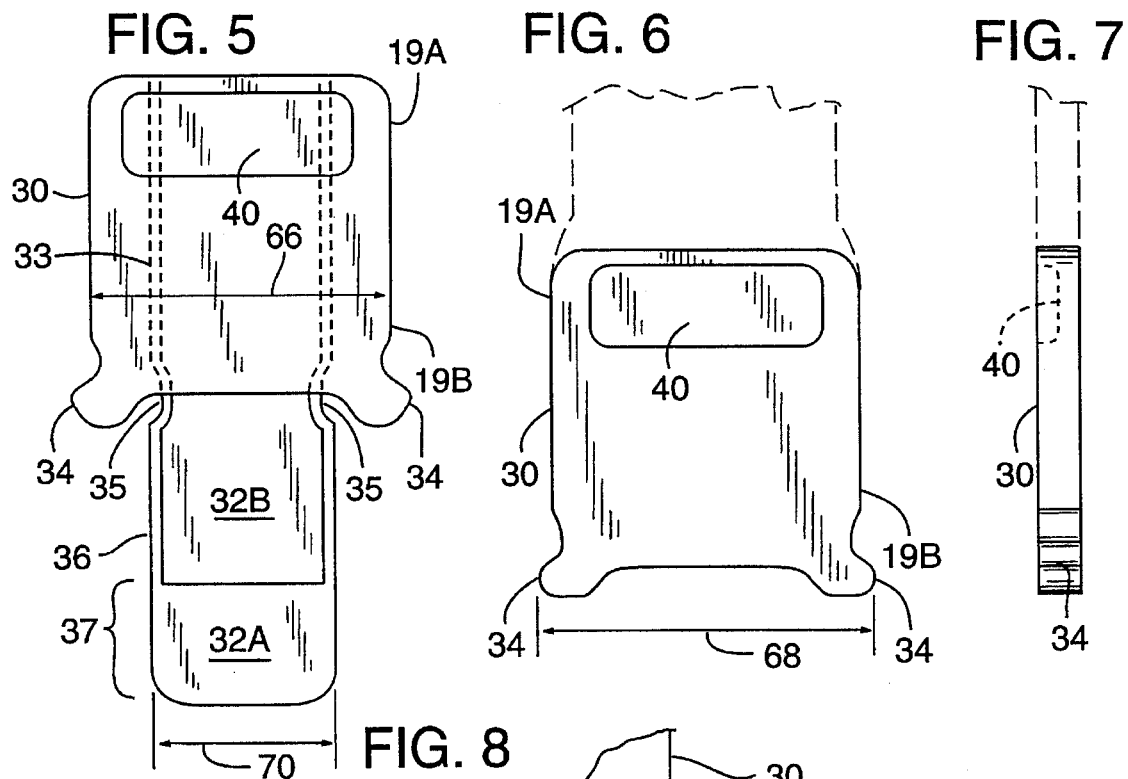

MINIATURE SELF-LOCKING LABIAL BRACKET WITH CAM-RELEASE CLOSURE MEMBER

BACKGROUND OF THE INVENTION

This invention relates generally to orthodontic attachments and more particularly to an improved miniature ligatureless or automatic locking-type labial bracket.

BACKGROUND OF INVENTION

My prior U.S. Pat. No. 5,094,614 discloses a miniature self-locking bracket having a closure slot extending through both sides of the bracket body across an archwire slot for a closure member to secure an archwire. The closure member ends are contained within the closure slot, and the bracket body has an internal shoulder extending across one side of the closure slot. The closure member is a lengthwise-folded flat spring having a free end positioned near one end and biased to engage the shoulder when closed. A locking tab cooperates with the free end to lock the closure member closed. Depressing the free end allows it to pass through an escape notch in the internal shoulder to slide the closure member to an open position. Intermediate ears positioned near the opposite end of the closure member engage the shoulder when open. The free end of the closure member springs outward to hold the member open.

While this basic self-locking bracket design is very effective, I have identified a number of improvements that facilitate fabrication and operation of the bracket.

SUMMARY OF THE INVENTION

It is, therefore, an object of the invention to improve my self-locking bracket so that it is easier to make and use.

Another object of the invention is to simplify the structure of the closure member of the self-locking bracket so that it is easier to fabricate in a reliable form.

A further object of the invention is to improve the structure of the closure member of the self-locking bracket so that it is easier to open when mounted on a patient's tooth.

The present invention is a self-locking orthodontic bracket having a closure member structure which is improved in several respects. In general, as in the case of my prior self-locking bracket, the bracket includes a bracket body, mountable on a tooth, having first and second side portions spaced apart to define an archwire slot for receiving an archwire. The bracket includes a closure slot which extends transversely over the archwire slot in the bracket body and a closure member receivable within the closure slot and slidable across the archwire slot. The closure slot includes a first slot portion formed in the first side portion of the bracket body and a second slot portion formed in the second side portion of the bracket body on opposite sides of the archwire slot. The closure member can thus be slid to a closed position through the first slot portion transversely of the archwire slot with an end portion inserted into the second slot portion to retain the archwire in the archwire slot. The bracket body and closure member include first locking means for releasably locking the closure member in said closed position in the closure slot and second locking means for locking the closure member in an open position in the closure slot to insert or remove the archwire.

In a preferred embodiment, the first slot portion includes means defining an internal shoulder oriented normal to the direction of closure of the closure member. The closure member includes a folded flat spring member having a free end biased outward to engage the internal shoulder to define said first locking means when the closure member is in the closed position and an intermediate retention ear positioned to engage the internal shoulder to define said second locking means when the closure member is in the open position. The closure member includes a flat core member with the flat spring member wrapped lengthwise around the core member.

One improvement according to the present invention is the addition, to the closure member, of camming release means for releasing the first locking means responsive to exertion of a force lengthwise of the closure member. In the preferred embodiment, the camming release means includes a ramp or linear cam formed in the free end of the flat spring member biased outward to engage the internal shoulder at an angle. Preferably, the flat core member has a recess or relief pocket for receiving the linear cam to facilitate clearance during lengthwise movement of the closure member. Pushing the closure member lengthwise in the slot with sufficient force causes the ramp to displace the free end away from the internal shoulder to disengage it. The user can, therefore, release and open the closure member with a single motion, rather than having to use one tool to disengage the closure member and another at the same time to push the closure member lengthwise in the slot. Also, the internal shoulder in the bracket body can be formed with a simpler, generally square cross-sectional structure rather than an L-shaped structure, which simplifies fabrication.

Another improvement according to the invention is to form the flat spring member in two layers, which increases its resiliency, and to wrap it only once around the core member, without overlapping its ends, which simplifies fabrication of the spring member. A related improvement is to form the second locking means in the core member, in the form of laterally-protruding ears, rather than in the flat spring member.

A further feature of the invention is implementation of the foregoing or other slider-type closure structures in combination with a twin-wing structure. This combination provides a dual mode structure that gives the orthodontist a versatile set of alternative or redundant means for securing an archwire in the archwire slot.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIG. 3 is a side elevation view of the assembled closure member of FIGS. 1 and 2 before insertion into the bracket body.

FIG. 4 is a perspective view of the closure member of FIG. 3.

FIG. 5 is a plan view of the assembled closure member in an unfolded condition at an intermediate step in its fabrication.

FIG. 6 is a plan view to scale of the core of the closure member before assembly into the structure of FIG. 5.

FIG. 7 is a side elevation view of the core as shown in FIG. 4, with the relief pocket half-etched in dashed lines.

FIG. 8 is an enlarged plan view showing details of an ear portion of the core of the closure member.

DETAILED DESCRIPTION

Figure 1:
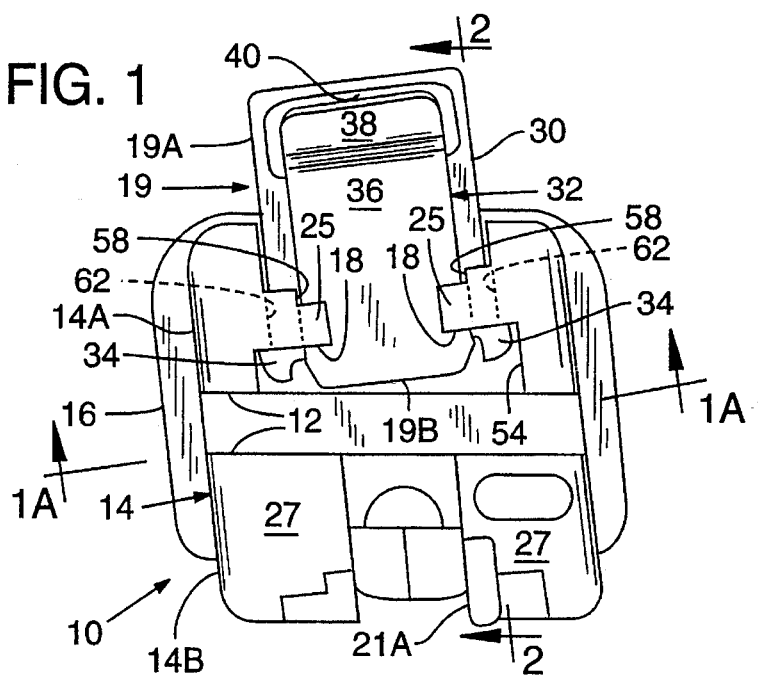
FIG. 1 is a front plan view, shown to scale, of an improved miniature self-locking bracket according to the invention, with the closure member in the open position.
Figure 2:
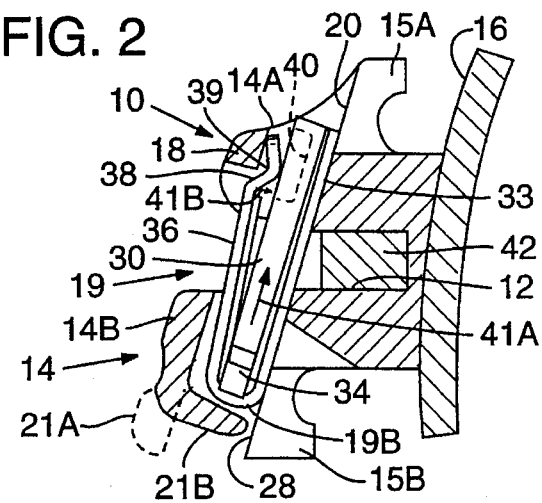
FIGS. 2 and 2A are cross-sectional views of the bracket body taken along lines 2—2 in FIG. 1 with an archwire shown in cross-section in the archwire slot, with the closure member shown in a closed position in FIG. 2 and in a half open position in FIG. 2A.
Figure 2A:
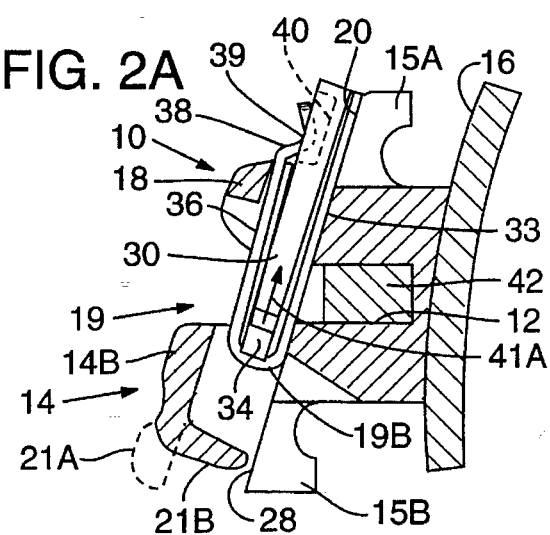

FIGS. 1, 2 and 2A show an improved miniature self-locking orthodontic bracket 10 according to a presently-preferred embodiment of the invention. The bracket comprises a bracket body 14 mounted on a pad 16 arranged for mounting on a tooth. The pad can be a foil mesh, perforated or other form of bonding pad concavely formed to fit a convex surface of a tooth, or it can be a band.

The bracket body has first and second lengthwise (inciso-gingival) side portions 14A, 14B spaced apart to define an archwire slot 12 for receiving an archwire 42. The bracket body preferably includes twin pairs of tie wings 15A, 15B. The archwire slot 12 preferably has a rectangular profile. The slot is preferably sized for edgewise techniques; that is, its depth is greater than its width for receiving an archwire in an edgewise position. It can also be angled, as known in the art so that the plan view of the overall bracket (FIG. 1) presents a parallelogram shape, to assist the orthodontist in bracket placement.

The bracket body 14 can be positioned on the pad 16 so that the archwire slot 12 is generally oriented for insertion and removal of the archwire in a labio-lingual direction, but slot 12 is preferably angled from a plane normal to the bonding pad as described by Andrews. The remainder of this description assumes the orientation shown in the drawing Figures. The invention can be used in an alternative orientation, however, with the archwire slot oriented for insertion and removal of the archwire in an inciso-gingival direction, that is, generally parallel to the bonding pad.

As shown in FIGS. 1, 2 and 2A, a closure member or slider 19 fits into an open-ended closure slot 20, 28 and is slidable transversely over the archwire slot 12 to retain the archwire 42 securely in the bracket body 14. The closure member is generally flat, wide and rectangular in shape, having a first end 19A and a second end 19B.

The closure member is sized to a length relative to slot 20, 28 such that, when the closure member is closed, the ends 19A, 19B are substantially flush with opposite outer sides of the bracket body. The closure member's shape provides a substantial area of contact between the closure member and the archwire for retaining the archwire in shear. The closure member preferably has a mesio-distal width substantially greater than its thickness (its labio-linual dimension in the drawing Figures) and substantially greater than the width of the archwire slot 12. The closure slot 20, 28 preferably has a cross-sectional mesio-distal to labio-lingual aspect ratio of at least 3:1, and more preferably about 5:1. A preferred construction of member 19 is further described below.

The closure slot includes a first lengthwise (inciso-gingival) slot portion 20 formed in the first side portion 14A of the bracket body and a second lengthwise (inciso-gingival) slot portion 28 formed in the second side portion 14B of the bracket body. The closure slot is open at opposite outer sides of the bracket body and has a generally T-shaped cross-sectional configuration. The closure slot is defined in the first side portion 14A of the bracket body by L-shaped opposed mirror-image arms 25 and in the second side portion 14B by L-shaped opposed mirror-image arms 27.

Thus, the closure member 19 and the closure slot portions 20, 28 are arranged so that the closure member can be slid transversely through the first slot portion 20 over the archwire slot from an open position (FIG. 1), through a half closed position (FIG. 2A), to a closed position (FIG. 2). In the open position (FIG. 1), the second end 19B of the closure member is retained in the first slot portion 20, with the archwire slot 12 open for insertion or removal of archwire 42. In the closed position (FIG. 2), the first end 19A of the closure member is retained within the first slot portion 20 and the second end 19B is within second slot portion 28 to retain the archwire 42 in shear.

As mentioned above, the bracket body includes a twin pair of tie wings 15A, 15B, one pair on each side of the closure slot. The use of twin tie wings is well-known in the art, but only in static brackets, not in an automatic or ligatureless bracket as in the present invention. The closure slot extends laterally over portions of the tie wings but does not impede their use by the orthodontist to apply elastic O-rings or tie wires around the wings and archwire. This arrangement gives the orthodontist a dual-mode closure structure. In cases in which the tooth and bracket are positioned such that the archwire cannot be initially captured in the archwire slot beneath the closure member, the orthodontist can secure the archwire using the tie wings and O-rings or tie wires. Also, having the closure mechanism spaced between the twin pairs of wings enables two adjacent brackets to be chained together. This aspect of the invention is not limited to use of the specific form of closure slot and rectangular closure member shown herein. It suffices to provide some form of guideway which need not be limited to a closed or partially closed slot and a closure member slidably conforming to the guideway for movement across the archwire slot to close the slot between the twin tie wings and thereby secure the archwire in the archwire slot when seated fully therein. When the archwire cannot seated fully in the archwire slot, the tie wings and ligature can be used in conventional fashion.

The bracket body includes a foldable locking tab, shown in dashed lines as tab 21A and in solid lines as tab 21B, on side portion 14B, bent down after insertion of the closure member to block retraction of the closure member through closure slot portion 28. The foldable locking tab 21A is formed above tie wing 15B when the bracket body is cast, in an open position as shown in dashed lines in FIG. 2. It is bent toward tie wing 15B, to the position of tab 21B shown in solid lines in FIG. 2, after insertion of the closure member to the closed position. The bendable tab on the bracket body, when bent down to the position of tab 21B, blocks the closure member from removal from the closure slot via slot portion 28. It thus serves the same purpose as the bendable locking tab on the core of the closure member in my prior patent but does so more simply in terms of fabrication. In combination with retention ears or stop tabs 34, further described below, these features serve to capture the closure member in the closure slot while leaving the closure member movable between open and closed positions, to place, hold and remove the archwire 42 in slot 12.

If the bracket body is mounted on a bonding pad so that the archwire slot 12 is oriented depthwise in an inciso-gingival direction, rather than labio-lingually as shown in the drawing figures, the bonding pad would provide alternative blocking means extending across the closure slot portion 28 for engaging an end of the closure member to retain the closure member in the closure slot.

The bracket body and closure member include first locking means for releasably locking the closure member in the closed position and second locking means for locking the closure member in an open position in the closure slot to insert or remove the archwire, as further described below. More specifically, as shown in FIG. 2, the first side portion 14A of the bracket body includes means, formed by inwardly-opposed extensions of arms 25, defining internal shoulders 18, for engaging the free end 36 of spring 32 to lock the closure member 36 in the closed position. Each shoulder 18 has a generally rectangular cross-sectional shape defined by a side face oriented normal to the direction of movement of the closure member lengthwise in the closure slot (arrow 41A) and a bottom face parallel to said direction of movement.

The closure member 19, in turn, has structure next described for abutting against the side face of shoulder 18 to lock the closure member in the aforementioned open and closed positions, as well as cammingly releasing it from the closed position responsive to sufficient lengthwise force. Because of the improved shape of the free end 36 of the flat spring 32, as next described, a generally rectangular cross-sectional shape of shoulder 18 is preferred. An L-shaped or concave structure as shown in my prior patent is unnecessary to hold the free end in its locking position against the outward bias of the flat spring.

The closure member 19 shown in FIGS. 1, 2 and 2A is a multilayer structure. As shown in further detail in FIGS. 3 and 4, this structure includes a thick (e.g., 0.010 inch) flat core or filler 30 having a flat spring member 32 wrapped or folded lengthwise around the core 30. The flat spring member 32 is preferably formed by an thin (e.g., 0.003 inch) outer spring member 32A and a thinner (e.g., 0.002 inch) inner spring member 32B. Preferably each spring layer 30, 32A, 32B is made of either 301 full hard stainless steel spring stock or 17-7 heat-treatable stainless steel. The flat spring member 32A, 32B is wrapped around two sides and one end of the core 30 and preferably has one portion 33 affixed to the side of the core member facing the archwire slot 12 (the lingual side) by means of spot welding. On the side of the core 30 opposite the archwire slot (the labial side), the spring member 32 has a free end or locking arm 36 which is biased outward (labially) at an acute angle (e.g., 30 degrees) from the core member 30. This arrangement enables the free end 36 to engage the internal shoulder 18 at the corner formed by the side and bottom faces thereof to define the first locking means when the closure member is in the closed position as shown in FIG. 2.

Figure 1A:
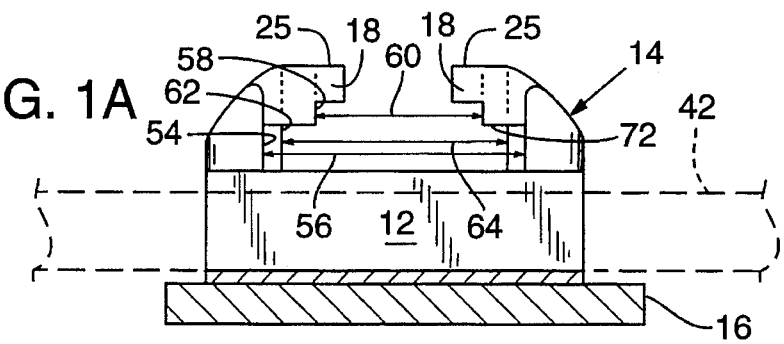
FIG. 1A is a cross-sectional view taken along line 1A—1A in FIG. 1, shown without the closure member to show the spacings of the closure slot portions.

The closure slot portions 20, 28 have a cross-sectional profile defined by a mirror-symmetric pair of steps as shown in FIG. 1 and 1A. These steps are arranged to form, in lengthwise slot portion 28 and part of portion 20 adjoining the archwire slot, a first or lower cross-sectional slot portion 54 adjoining the archwire slot 12 and having a first width 56, and a second or upper cross-sectional slot portion 58 spaced labially from the archwire slot by the first cross-sectional slot portion and having a second width 60 less than the first width 56. In lengthwise slot portion 20, the lower slot portion has a lengthwise subportion 62 having a reduced width 64 less than the width 56.

The core member 30 of the closure member has a first width 66 (FIG. 5) sized slightly less than the reduced width 64 of the lengthwise portion 62 of the first slot portion to fit slidably within the first slot portion. The retention ears 34 have a lateral width 68 (FIG. 6) less than the width 56 of the first cross-sectional slot portion 54, to permit initial insertion of the closure member in lengthwise slot portions 20 and 28, but less than the reduced width 64 of lengthwise subportion 62 to prevent removal of the closure member from slot portions 20 when in the opened position. The free end 36 of the flat spring member has a second width 70 (FIG. 5) less than the width 66 of the core portion, sized to fit slidably within the width 60 second slot portion 58. The core member 30 thus engages the undersurfaces 72 of the arms 25 to support the entire shearing force exerted by the archwire when the closure member is closed.

Referring to FIG. 5, the inner layer 32B of the flat spring member is slightly narrower than the outer layer 32A, and is also somewhat shorter, terminating just short of a distal end portion 37 of the outer layer. The inner and outer layers 32A, 32B are formed in parallel-sided strips with opposed mirror image notches 35 aligned along opposite sides thereof approximately midway between the ends of outer layer 32A, to facilitate positioning and bending the layer 32A, 32B around one end 19B of the core 30. The spring layers 32A, 32B are secured along their lower sides 33 to the core member 30 by welding or brazing.

The distal end portion 37 (FIG. 5) of the outer layer 32A is formed in a recurved shape. This recurved shaped is designed to provide a ramp portion 38 angled (angle 50) toward the core 30 from the principal plane of free end 36. This ramp serves to engage shoulder 18 when the closure member is in the closed position (FIG. 2) and also to cammingly release the free end to unlock the closure member (FIG. 2A). Preferably, but not essentially, the distal end portion also includes a terminal retainer portion 39 which is angled (angle 52) in the opposite direction from ramp portion 38 back toward or past the principal plane of free end 36.

The ramp portion 38 abuts against shoulder 18 when the closure member is in the closed position to releasably lock it in the closure slot over the archwire slot. The labial surface of the ramp portion 38 is angled at an obtuse angle 50, e.g., at 30 to 60 degrees from the principal plane of free end 36 (this angle is the supplementary angle of angle 50 shown in FIG. 3, which is, for example, 120 to 150 degrees from the principal plane of free end 36). Therefore, when sufficient force is exerted lengthwise of the closure member (arrow 41A), the labial surface of the ramp portion cammingly engages against internal shoulder 18 to deflect the free end 36 'toward core 30 (arrow 41B) to provide a camming release of the locking arm from abutment with shoulder 18. During release of the locking arm, the free end 36 is first deflected toward core 30 until ramp portion 38 clears the shoulder 18 (FIG. 2). Then the labial surface of the free end slides freely along the bottom side of shoulder 18 (FIG. 2A).

The terminal retainer portion 39 is angled in the opposite direction from ramp portion 38 at an obtuse angle 52 (e.g., at 45 to 75 degrees from ramp portion 38), preferably to a position about parallel to the principal plane of free end 36. The terminal retainer portion 39 extends in length a sufficient distance past the corner of shoulder 18 when the closure member is closed to retain the free end 36, which is biased away from core 30, captured beneath arms 25.

The core 30 of the closure member is generally rectangular in shape, as shown in FIGS. 5 and 6, with a length sufficient to span the arch wire slot when closed, for example, 0.090 inch. At one end, the core has retention ears or stop tabs 34 protruding laterally (mesio-distally) in opposite directions. The stop tabs 34 are formed in a mirror image of one another, and have a span slightly greater than the width of the portion of the closure slot beneath arms 25. The remainder of the closure slot has a width sufficient to accommodate the widthwise span of tabs 34. For example, the width of the core 30 can be 0.079 inch and the tabs 34 can have a span of 0.089 inch.

As shown in FIG. 6 and 7, the core 30 has a relief pocket 40, positioned near the end 19A of core 30 opposite stop tabs 34 to receive the distal end portion 37 of outer spring layer 32A. The relief pocket 40 is preferably chemically etched (half-etched) to a depth of about half the thickness of the core member (a depth of 0.004–0.006 inch). Alternatively, the core member could be formed of two layers sandwiched together, with pocket 40 formed in one layer. The dashed lined portions of core 30 shown in FIGS. 6 and 7 at an intermediate stage of production indicate a carrier strip that is used during assembly and then cut off.

The relief pocket 40 has a length and width slightly greater than the length and width of the recurved distal end portion 37 of outer spring layer 32A. For example, the width of the relief pocket (its larger dimension) can be about 0.58 inch, which is wider than the outer spring layer 32A (see FIG. 3). The relief pocket helps to retain the recurved shape of the distal end portion 37 when deflected against the core 30 to unlock the closure member as shown in FIG. 2A.

Sufficient core material should be retained on opposite lateral sides of the pocket 40 to withstand the shearing forces of holding the archwire in the archwire slot when the closure member is in the closed position. Because of the differing widths of the upper and lower cross-sectional slot portions, the core bears substantially the entire shearing force applied by the archwire on bracket body surfaces 72. The free end of the spring thereby remains free to operate independently of the shearing forces during opening and closing.

The bracket body 14 is preferably made by casting or powdered melding forming techniques but can be formed by other techniques, such as laminating pre-etched layers together or numerically-controlled machining. The spring layers 32A, 32B can be formed by die stamping, during which distal portion 37 of layer 32A can be shaped as described above, or can be chemically-etched and then shaped in a secondary operation.

The resultant bracket is used in a manner well known in the art. Like my prior bracket, it has the advantage of being lockable to hold an archwire in the archwire slot without a tie wire or elastomer O-ring, although this embodiment permits the addition of such ligatures. It has the further advantages of ease of opening the closure member when closed (FIG. 2A), and retaining the closure member in the bracket when opened (FIG. 1). The closure member design is easier to open when opening is intended, and less likely to be damaged in the process. Moreover, the design makes it easier to fabricate the bracket body.

Having described and illustrated the principles of the invention in a preferred embodiment thereof, it should be apparent that the invention can be modified in arrangement and detail without departing from such principles. I claim all modifications and variation coming within the spirit and scope of the following claims.

We claim:

1. An improved self-locking orthodontic bracket mountable on a tooth, the bracket comprising:

a bracket body having first and second side portions spaced apart to define an archwire slot for receiving an archwire;

a closure slot extending transversely of the archwire slot in the bracket body;

a closure member receivable within the closure slot and slidable across the archwire slot;

the closure slot including a first lengthwise slot portion formed in the first side portion of the bracket body and a second lengthwise slot portion formed in the second side portion of the bracket body on opposite sides of the archwire slot so that the closure member can be slid to a closed position through the first lengthwise slot portion transversely of the archwire slot with an end portion inserted into the second slot portion to retain the archwire in the archwire slot;

the first lengthwise slot portion including an internal shoulder oriented normal to the direction of closure of the closure member and the closure member including a folded flat spring member having a free end biased outward to engage the internal shoulder and thereby lock the closure member in the closed position;

the free end of the folded flat spring member including a cam responsive to exertion of a force lengthwise of the closure member for deflecting the free end away from the internal shoulder to unlock the closure member;

the closure member including a flat core member having a relief pocket positioned adjacent the cam to receive a camming portion of the free end when the free end is deflected away from the internal shoulder to unlock the closure member.

2. A bracket according to claim 1 in which the closure member includes a flat core member having an intermediate retention ear protruding laterally to engage the bracket body on opposite lateral sides of the first lengthwise slot portion to retain the closure member in an open position.

3. A bracket according to claim 1 in which the bracket body includes blocking means extending across the closure slot for engaging an end of the closure member to retain the closure member in the closure slot.

4. A bracket according to claim I in which the closure slot has a cross-sectional profile defined by a mirror-symmetric pair of steps spaced to form a first cross-sectional slot portion having a first width and a second cross-sectional slot portion having a second width less than the first width, the closure member including a flat core member having a first width sized to fit slidably within the first cross-sectional slot portion and the free end of the flat spring member having a second width less than the width of the core portion and sized to fit slidably within the second cross-sectional slot portion.

5. A bracket according to claim 1 in which the free end of the folded flat spring member includes a distal end portion which is recurved to form a ramp portion angled at an obtuse angle in a first direction from a principal plane of the flat spring member to define said cam and a terminal retainer portion which is angled in an opposite direction from the ramp portion back toward the principal plane of the flat spring member and having a length sufficient to extend beneath the internal shoulder to retain the free end beneath the internal shoulder when the closure member is closed.

6. An improved self-locking orthodontic bracket mountable on a tooth the bracket comprising:

a bracket body having first and second side portions spaced apart to define an archwire slot for receiving an archwire;

a closure slot extending transversely of the archwire slot in the bracket body;

a closure member receivable within the closure slot and slidable across the archwire slot;

the closure slot including a first lengthwise slot portion formed in the first side portion of the bracket body and a second lengthwise slot portion formed in the second side portion of the bracket body on opposite sides of the archwire slot so that the closure member can be slid to a closed position through the first lengthwise slot portion transversely of the archwire slot with an end portion inserted into the second slot portion to retain the archwire in the archwire slot:

the first lengthwise slot portion including an internal shoulder oriented normal to the direction of closure of the closure member and the closure member including a folded flat spring member having a free end biased outward to engage the internal shoulder and thereby lock the closure member in the closed position;

the free end of the folded flat spring member including a cam responsive to exertion of a force lengthwise of the closure member for deflecting the free end away from the internal shoulder to unlock the closure member:

the bracket body including a pair of tie wings extending in opposite directions from the archwire slot alongside the closure slot for holding a tie wire or O-ring across the archwire slot.

7. An improved self-locking orthodontic bracket mountable on a tooth, the bracket comprising:

a bracket body having first and second side portions spaced apart to define an archwire slot for receiving an archwire;

a closure slot extending transversely of the archwire slot in the bracket body;

a closure member receivable within the closure slot and slidable across the archwire slot;

the closure slot including a first lengthwise slot portion formed in the first side portion of the bracket body and a second slot portion formed in the second side portion of the bracket body on opposite sides of the archwire slot so that the closure member can be slid to a closed position through the first lengthwise slot portion transversely of the archwire slot with an end portion inserted into the second slot portion to retain the archwire in the archwire slot;

the first lengthwise slot portion including an internal shoulder oriented normal to the direction of closure of the closure member and the closure member including a folded flat spring member having a free end biased outward to engage the internal shoulder to lock the closure member in the closed position;

the closure member including a flat core member having an intermediate retention ear protruding laterally to engage the bracket body on opposite lateral sides of the first lengthwise slot portion to retain the closure member in an open position;

the bracket body including a pair of tie wings extending in opposite directions from the archwire slot alongside the closure slot for holding a tie wire or O-ring across the archwire slot.

8. A bracket according to claim 7 in which a distal end portion of the flat spring member is angled at an obtuse angle from a principal plane of the flat spring member to form a ramp portion defining a cam.

9. A bracket according to claim 8 in which the closure member includes a flat core member having a relief pocket positioned to receive the distal end portion including the ramp portion when the free end is deflected away from the internal shoulder to unlock the closure member.

10. A bracket according to claim 7 in which the bracket body includes a blocking member extendable across the closure slot to abut an end of the closure member and thereby retain the closure member in the closure slot.

11. A bracket according to claim 7 in which the closure slot has a cross-sectional profile defined by a mirror-symmetric pair of steps spaced to form a first cross-sectional slot portion having a first width and a second cross-sectional slot portion having a second width less than the first width, the closure member including a flat core member having a first width sized to fit slidably within the first cross-sectional slot portion and the free end of the flat spring member having a second width less than the width of the core portion sized to fit slidably within the second cross-sectional slot portion, the retention ears having a lateral width greater than the first width of the core member.

12. A bracket according to claim 11 in which the width of the retention ears is greater than the width of the first cross-sectional slot portion in a subportion of the first lengthwise slot portion to prevent removal of the closure member from the slot when in the opened position, but less than the width of the first cross-sectional slot portion in second lengthwise slot portion to permit initial insertion of the closure member.

13. An improved self-locking orthodontic bracket mountable on a tooth, the bracket comprising:

a bracket body having first and second side portions spaced apart to define an archwire slot for receiving an archwire;

a closure slot extending transversely of the archwire slot in the bracket body;

a closure member receivable within the closure slot and slidable across the archwire slot;

the closure slot including a first lengthwise slot portion formed in the first side portion of the bracket body and a second slot portion formed in the second side portion of the bracket body on opposite sides of the archwire slot so that the closure member can be slid to a closed position through the first lengthwise slot portion transversely of the archwire slot with an end portion inserted into the second slot portion to retain the archwire in the archwire slot;

the first lengthwise slot portion including an internal shoulder oriented normal to the direction of closure of the closure member and the closure member includes a folded flat spring member having a free end biased outward to engage the internal shoulder to lock the closure member in the closed position;

the bracket body including a block positionable across the closure slot for engaging an end of the closure member to retain the closure member in the closure slot;

the bracket body including a pair of tie wings extending in opposite directions from the archwire slot alongside the closure slot for holding a tie wire or O-ring across the archwire slot.

14. A bracket according to claim 13 in which the block comprises a tab formed in the bracket body, the tab protruding lengthwise of the closure slot and bendable across the closure slot to engage an end of the closure member to block the closure member from removal from the closure slot.

15. A bracket according to claim 13 in which the closure slot has a cross-sectional profile defined by a mirror-symmetric pair of steps spaced to form a first cross-sectional slot portion having a first width and a second cross-sectional slot portion having a second width less than the first width, the closure member including a flat core member having a first width sized to fit slidably within the first cross-sectional slot portion and the free end of the flat spring member having a second width less than the width of the core portion sized to fit slidably within the second cross-sectional slot portion, the closure member including a pair of retention ears protruding laterally in opposite directions and having a lateral width greater than said first width of the core member.

16. A bracket according to claim 15 in which the width of the retention ears is greater than the width of a subportion of the first cross-sectional slot portion in the first lengthwise slot portion to prevent removal of the closure member from the closure slot when in the opened position, but less than the width of the first cross-sectional slot portion in a second lengthwise slot portion to permit initial insertion of the closure member.

17. An improved self-locking orthodontic bracket mountable on a tooth, the bracket comprising:

a bracket body having first and second side portions spaced apart to define an archwire slot for receiving an archwire;

a first pair of tie wings extending in opposite directions from the archwire slot for holding a tie wire or O-ring across the archwire slot over the archwire;

a second pair of tie wings extending in opposite directions from the archwire slot for holding a tie wire or O-ring across the archwire slot;

the first and second pairs of tie wings being spaced apart along opposite sides of the archwire slot;

a guideway formed in the bracket body extending across the archwire slot above the first and second pairs of tie wings; and a closure member slidable along the guideway over the archwire slot above the first and second pairs of tie wings to secure the archwire in the archwire slot when the archwire is fully seated therein;

the pairs of tie wings serving as an alternative means for securing the archwire in the slot with a tie wire or O-ring when the archwire cannot be fully seated therein.

18. A bracket according to claim 17 in which the guideway comprises a closure slot extending transversely of the archwire slot in the bracket body and the closure member comprises a generally rectangular member sized and arranged to be slidably received within the closure slot to secure the archwire therein under shear.

19. A bracket according to claim 18 in which the closure slot includes a first lengthwise slot portion formed in the first side portion of the bracket body and a second lengthwise slot portion formed in the second side portion of the bracket body on opposite sides of the archwire slot so that the closure member can be slid to a closed position through the first lengthwise slot portion transversely of the archwire slot with an end portion inserted into the second slot portion to retain the archwire in the archwire slot;

the first lengthwise slot portion including an internal shoulder oriented normal to the direction of closure of the closure member and the closure member including a folded flat spring member having a free end biased outward to engage the internal shoulder to lock the closure member in the closed position.

20. A bracket according to claim 18 in which the bracket body includes a block extendable across the closure slot for engaging an end of the closure member to retain the closure member in the closure slot.

* * * * *